(12) United States Patent
Djupesland et al.

(10) Patent No.: US 10,179,216 B2
(45) Date of Patent: Jan. 15, 2019

(54) NASAL DELIVERY DEVICES

(71) Applicant: OPTINOSE AS, Oslo (NO)

(72) Inventors: Per Gisle Djupesland, Oslo (NO);
Kate Dudgeon, Providence, RI (US);
Joseph Gordon, Mansfield, MA (US);
Mark Guarraia, Cranston, RI (US);
Michael Leclerc, Cranston, RI (US);
Ramy A Mahmoud, Skillman, NJ (US)

(73) Assignee: OptiNose AS, Oslo (NO)

( * ) Notice: Subject to any disclaimer, the term of this patent is extended or adjusted under 35 U.S.C. 154(b) by 133 days.

(21) Appl. No.: 14/380,836

(22) PCT Filed: Feb. 25, 2013

(86) PCT No.: PCT/EP2013/053748
§ 371 (c)(1),
(2) Date: Aug. 25, 2014

(87) PCT Pub. No.: WO2013/124493
PCT Pub. Date: Aug. 29, 2013

(65) Prior Publication Data
US 2015/0246194 A1    Sep. 3, 2015

Related U.S. Application Data

(60) Provisional application No. 61/603,089, filed on Feb. 24, 2012.

(51) Int. Cl.
*A61M 15/08*    (2006.01)
*A61M 15/00*    (2006.01)

(52) U.S. Cl.
CPC ........ *A61M 15/08* (2013.01); *A61M 15/0021* (2014.02); *A61M 2202/04* (2013.01);
(Continued)

(58) Field of Classification Search
CPC .............. A61M 15/0021; A61M 15/08; A61M 2202/04; A61M 2202/064;
(Continued)

(56) References Cited

U.S. PATENT DOCUMENTS 605,436 A    6/1898   Kellogg
642,748 A    2/1900   Manners
(Continued)

FOREIGN PATENT DOCUMENTS

CN    200994915    12/2007
CN    101918061    12/2010
(Continued)

OTHER PUBLICATIONS

Cindy H. Dubin, *Nothing to Sneeze At*, Pharmaceutical Formulation & Quality Magazine (Jan. 29, 2003).
(Continued)

*Primary Examiner* — Brandy S Lee
(74) *Attorney, Agent, or Firm* — Finnegan, Henderson, Farabow, Garrett & Dunner, LLP

(57) ABSTRACT

A nasal delivery device comprising: a housing (15); a nosepiece (17) for fitting to a nasal cavity of a subject; a mouthpiece (19) through which the subject in use exhales; and a substance supply unit (21) including an actuation member (23) which extends from one end of the housing and is manually actuated to deliver substance to the nasal cavity of the subject; wherein the housing includes a grip section (27) which is disposed at the one end of the housing from which the actuation member extends, said grip section comprising a first, distal part (28) including at least one projecting grip element (29) by which the subject grips the housing in actuating the actuation member, and a second, proximal part (31) providing a recess (33) in which fingers
(Continued)

Figure 1:
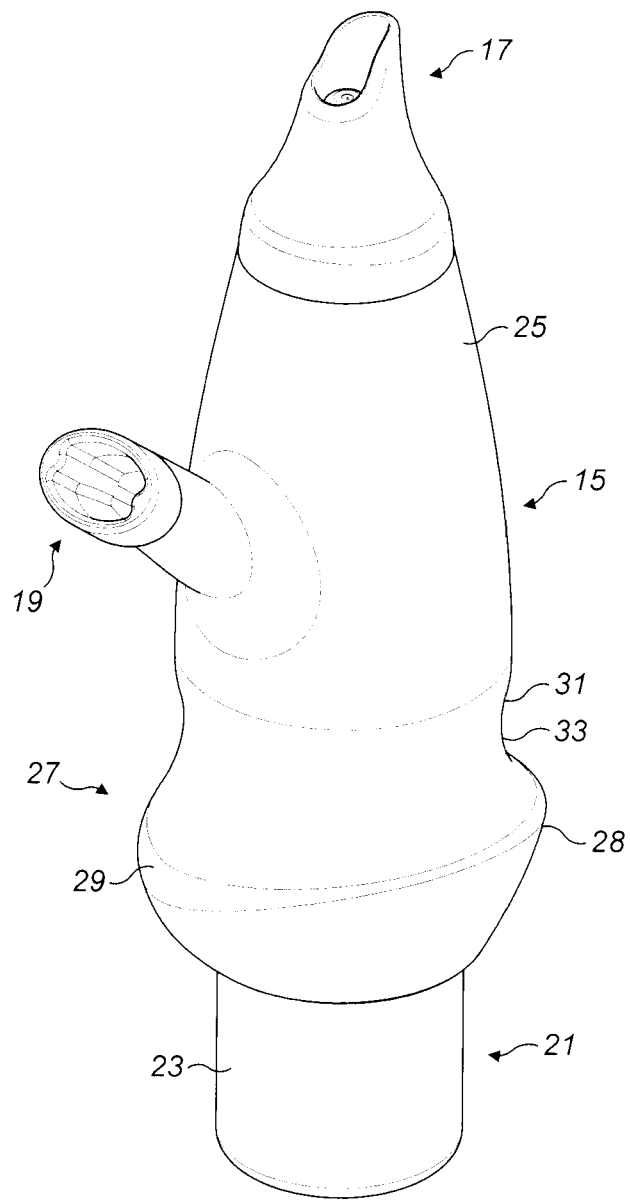

of the subject are located, said recess promoting proper orientation of the delivery device in a hand of the subject.

6 Claims, 5 Drawing Sheets

(52) U.S. Cl.
CPC . *A61M 2202/064* (2013.01); *A61M 2205/586* (2013.01); *A61M 2210/0618* (2013.01); *A61M 2210/0625* (2013.01)

(58) Field of Classification Search
CPC .... A61M 2205/586; A61M 2210/0618; A61M 2210/0625
See application file for complete search history.

(56) References Cited

U.S. PATENT DOCUMENTS

| | | |
|---|---|---|
| 746,749 A | 12/1903 | Seidel |
| 5,797,392 A | 8/1998 | Keldmann et al. |
| 6,648,848 B1 | 11/2003 | Keldmann et al. |
| 6,715,485 B1 | 4/2004 | Djupesland |
| D530,815 S | 10/2006 | Murphy et al. |
| 7,347,201 B2 | 3/2008 | Djupesland |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 6/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| 2002/0046751 A1* | 4/2002 | MacRae ............ A61M 15/0086 128/200.22 |
| 2004/0024330 A1 | 2/2004 | Djupesland et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0149289 A1 | 8/2004 | Djupesland |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0242959 A1 | 9/2010 | Djupesland et al. |
| 2010/0282246 A1 | 11/2010 | Djupesland et al. |
| 2010/0288275 A1 | 11/2010 | Djupesland et al. |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |

FOREIGN PATENT DOCUMENTS

| | | |
|---|---|---|
| GB | 2471973 | 1/2011 |
| JP | 2010/540147 | 12/2010 |
| RU | 2010117362 | 11/2011 |
| WO | WO 96/22802 | 8/1996 |
| WO | WO 98/53869 | 12/1998 |

(56) References Cited

FOREIGN PATENT DOCUMENTS

| | | |
|---|---|---|
| WO | WO 00/51672 | 9/2000 |
| WO | WO 01/78818 | 10/2001 |
| WO | WO 01/97689 | 12/2001 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/020350 | 3/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/067254 | 6/2008 |
| WO | WO 2008/081326 | 7/2008 |
| WO | WO 2008/081327 | 7/2008 |
| WO | WO 2008/122018 | 10/2008 |
| WO | WO 2008/122791 | 10/2008 |
| WO | WO 2008/122795 | 10/2008 |
| WO | WO 2009/044172 | 4/2009 |
| WO | WO2009044172 | * 4/2009 |
| WO | WO 2010/029441 | 3/2010 |
| WO | WO 2011/153406 | 12/2011 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

Per Gisle Djupesland, *Nasal Delivery of Vaccines*, EPC (Jan. 29, 2003).

Per Gisle Djupesland, *Who Nose How Far Nasal Delivery Can Go?*, EPC (Oct. 7, 2003).

Per Gisle Djupesland, *Bi-directional Nasal Drug Delivery*, Innovations in Pharmaceutical Technology (Jul. 10, 2004).

P.G. Djupesland, *Bi-Directional Nasal Delivery of Aerosols Can Prevent Lung Deposition*, Journal of Aerosol Medicine (Sep. 2004).

*Bi-Directional Nasal Device Delivers Drug on Exhalation*, Pharmaceutical Technology (Sep. 10, 2004).

Ola Dale et al., *Intranasal Midazolam: A Comparison of Two Delivery Devices in Human Volunteers*, Journal of Pharmacy and Pharmacology (Oct. 2004).

M. Kleven, *Using Computational Fluid Dynamics (CFD) to Improve the Bi-Directional Nasal Drug Delivery Concept*, Trans IChemE Part C. (Jun. 2005).

Per Gisle Djupesland, *Breath-Actuated Bi-Directional Delivery Sets the Nasal Market on a New Course*, ONdrugDelivery (Oct. 10, 2005).

Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).

P.G. Djupesland et al., *Breath Actuated Nasal Device Improves Delivery to Target Sites Beyond the Nasal Valve*, The Laryngoscope (Mar. 2006).

R. Luthringer et al., *Rapid Absorption of Sumatriptan Powder and Effects on Glyceryl tinitrate Model of Headache Following Intranasal Delivery Using a Novel Bi-Directional Device*, Journal of Pharmacy and Pharmacology (Jan. 2009).

A. Skretting et al., *A New Method for Scintigraphic Quantification of Deposition and Clearance in Anatomical Regions of the Human Nose*, Nuclear Medicine Communications (Aug. 2009).

Vlckovia et al., *Effective Treatment of Mild-to-Moderate Nasal Polyposis with Fluticasone Delivered by a Novel Device*, Rhinology (Oct. 22, 2009).

Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered by a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, *Nasal Deposition and Clearance in Man: Comparison of a Bidirectional Powder Device and a Traditional Liquid Spray Pump*, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The COMPASS Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

* cited by examiner

NASAL DELIVERY DEVICES

The present invention relates to a nasal delivery device for and a method of delivering substances, in particular one of a liquid, as a suspension or solution, or a powder, containing a medicament, especially systemic or topical pharmaceuticals, or a vaccine, to the nasal airway of a subject.

Figure 5:
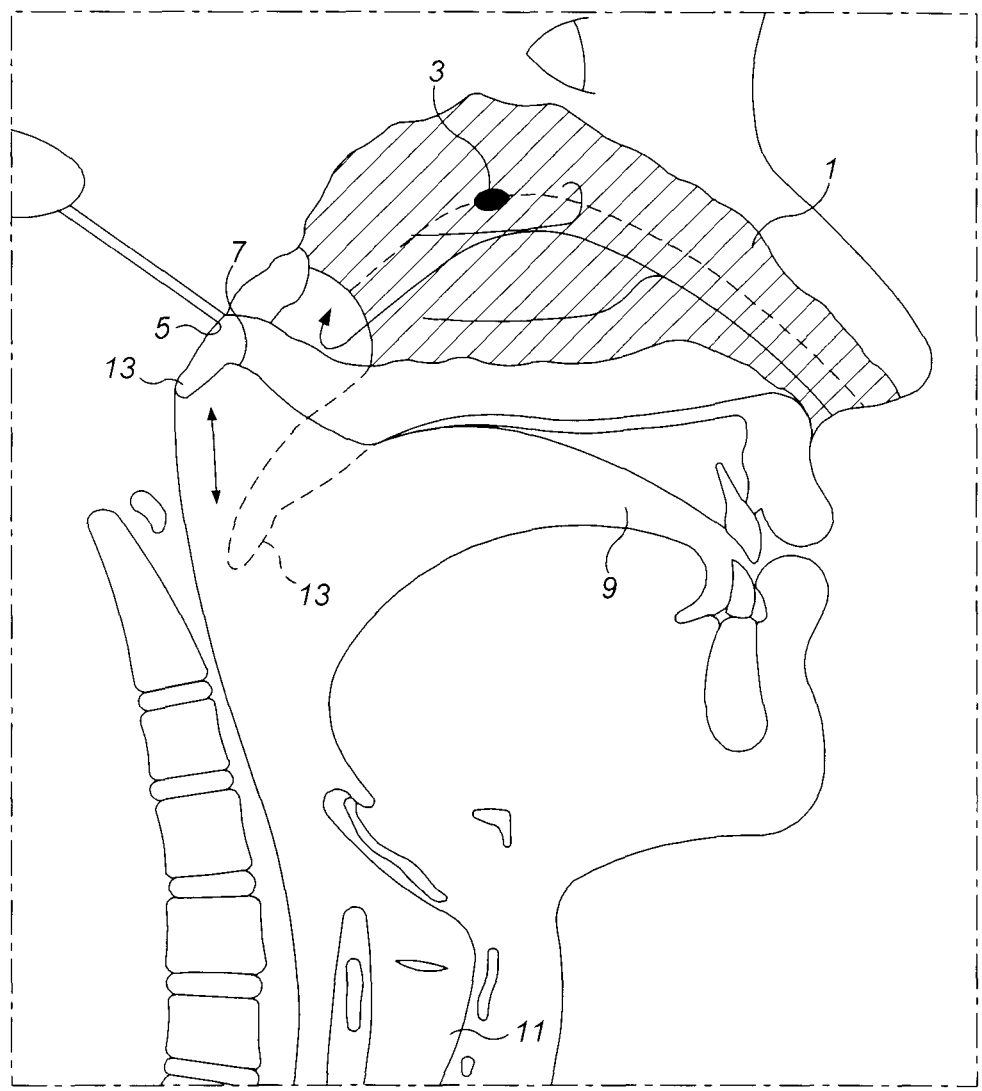

Referring to FIG. 5, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and anti-biotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements.

Currently, blood samples are most frequently used, but the analysis of molecules in the exhalation breath of subjects has been proposed as an alternative to blood analysis for several conditions. Breath analysis is currently used for the diagnosis of conditions such as helicobacter pylori infections which cause gastric ulcers.

WO-A-2000/051672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide nasal delivery devices and methods for delivering substances to a nasal cavity of subject, and in particular relatively-simple mechanically-actuatable delivery devices.

In one aspect the present invention provides a nasal delivery device for delivering substance to a nasal cavity of a subject, the delivery device comprising: a housing; a nosepiece for fitting to a nasal cavity of a subject; a mouthpiece through which the subject in use exhales; and a substance supply unit, which includes an actuation member which extends from one end of the housing and is manually actuated to deliver substance to the nasal cavity of the subject; wherein the housing includes a main body section, from one, base end of which extends the actuation member of the substance supply unit, and a grip section, which is disposed at the one end of the main body section, the grip section comprising a first, distal part which includes at least one projecting grip element by which the subject grips the housing in actuating the actuation member of the substance supply unit, and a second, proximal part which provides a recess in which fingers of the subject are located, whereby the recess promotes proper orientation of the delivery device in a hand of the subject.

In one embodiment the main body section comprises an elongate section.

In one embodiment the at least one projecting grip element is a circumferential lip which extends around or substantially around the periphery of the housing.

In another embodiment the distal part of the grip section comprises first and second projecting grip elements, which project to opposite sides of the housing, with no intermediate elements.

In one embodiment the first and second projecting grip elements are aligned on an axis common with that of the mouthpiece.

In another aspect the present invention provides a method of delivering substance to a nasal cavity of a subject, the method comprising the steps of: providing a nasal delivery device, comprising: a housing; a nosepiece for fitting to a nasal cavity of the subject; a mouthpiece through which the subject exhales; and a substance supply unit, which includes an actuation member which extends from one end of the housing and is manually actuated to deliver substance to the nasal cavity of the subject; wherein the housing includes a main body section, from one, base end of which extends the actuation member of the substance supply unit, and a grip section, which is disposed at the one end of the main body section, the grip section comprising a first, distal part which includes at least one projecting grip element by which the subject grips the housing in actuating the actuation member of the substance supply unit, and a second, proximal part which provides a recess in which fingers of the subject are located; fitting the nosepiece to the nasal cavity of the subject; locating the mouthpiece in the mouth of the subject; and gripping the housing such that fingers of the subject are located in the recess to opposite sides of the housing and adjacent the at least one projecting grip part, thereby promoting proper orientation of the delivery device in a hand of the subject to effect operation of the delivery device.

In one embodiment the main body section comprises an elongate section.

In one embodiment the at least one projecting grip element is a circumferential lip which extends around or substantially around the periphery of the housing.

In another embodiment the distal part of the grip section comprises first and second projecting grip elements, which project to opposite sides of the housing, with no intermediate elements.

In one embodiment the first and second projecting grip elements are aligned on an axis common with that of the mouthpiece.

Figure 2A:
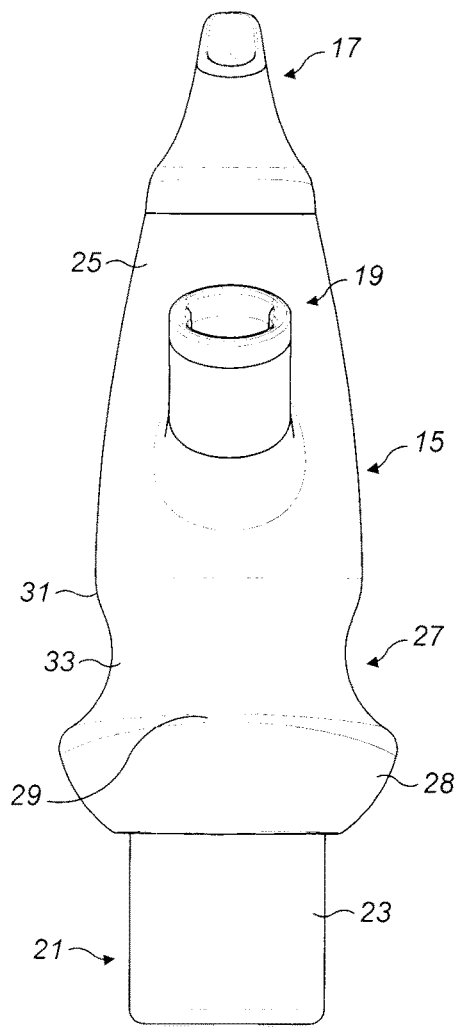
Figure 2B:
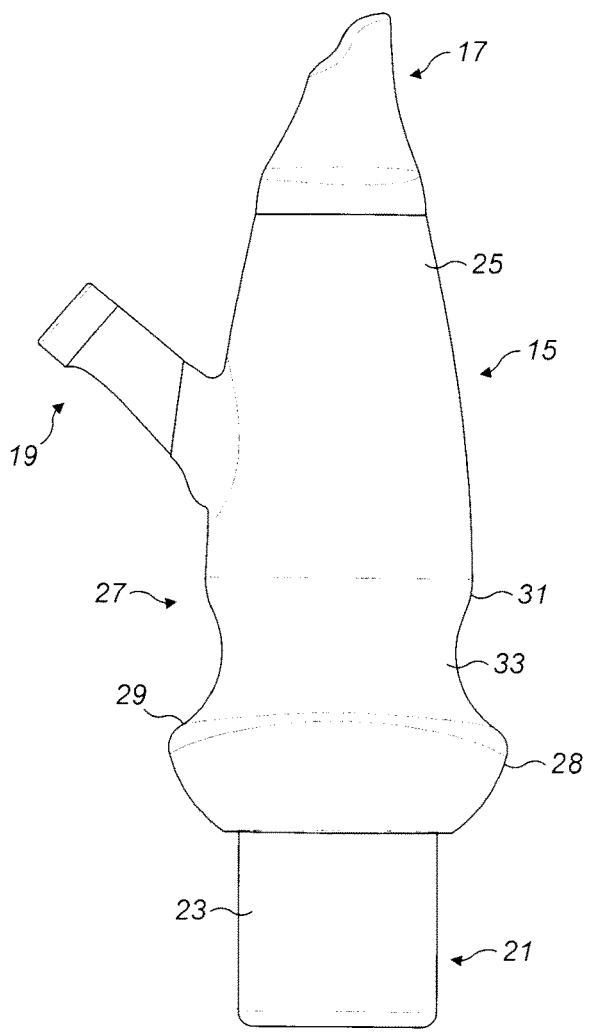
Figure 3:
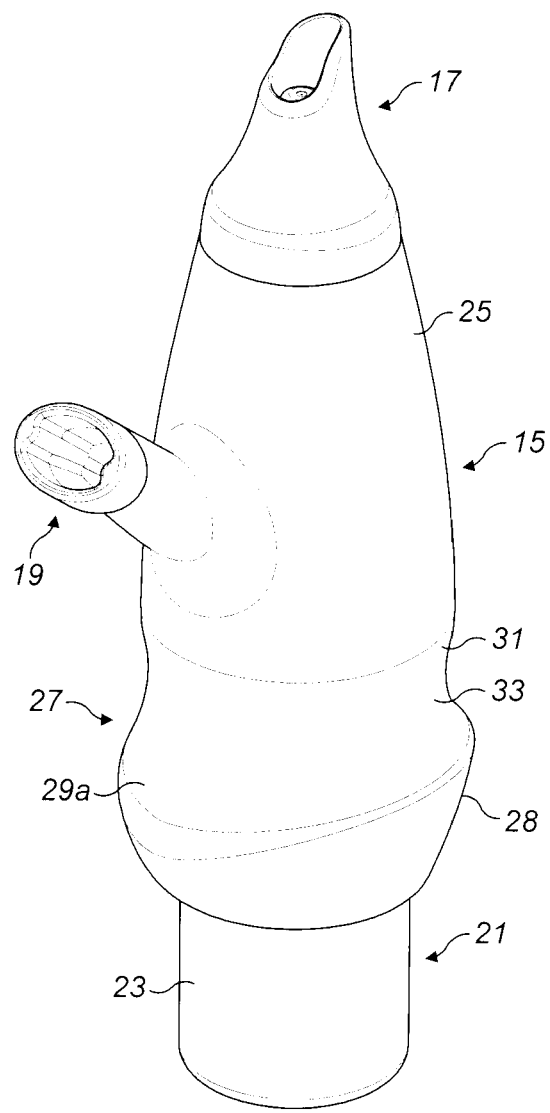
Figure 4A:
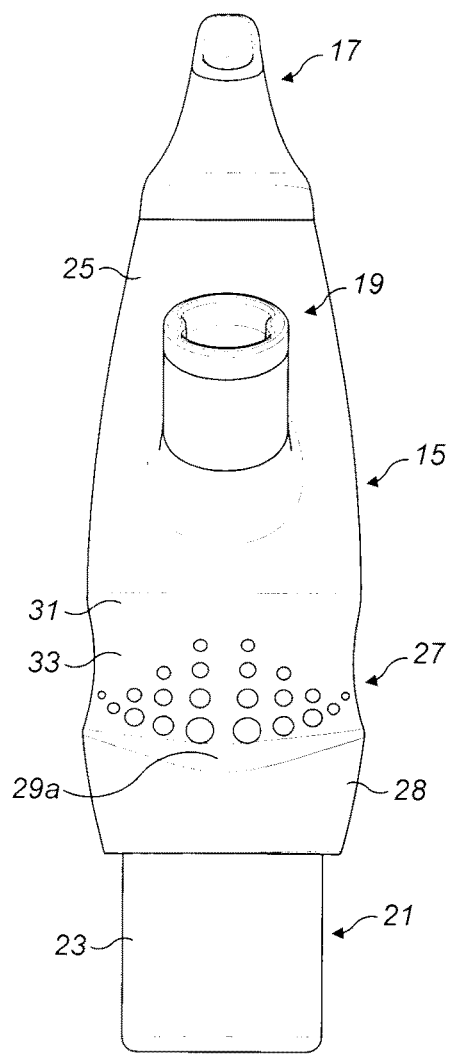
Figure 4B:
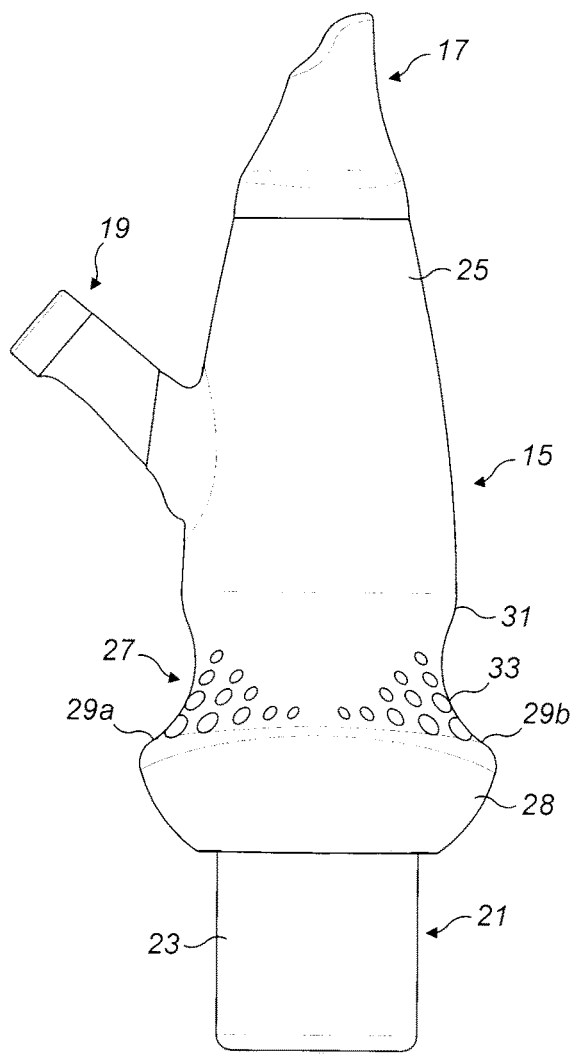

Preferred embodiments of the present invention will now be described hereinbelow by way of example only with reference to the accompanying drawings, in which:

FIG. 1 illustrates a perspective view of a nasal delivery device in accordance with a first embodiment of the present invention;

FIGS. 2(*a*) and (*b*) illustrate orthogonal side views of the delivery device of FIG. 1;

FIG. 3 illustrates a perspective view of a nasal delivery device in accordance with a second embodiment of the present invention;

FIGS. 4(*a*) and (*b*) illustrate orthogonal side views of the delivery device of FIG. 3; and FIG. 5 schematically illustrates the anatomy of the upper respiratory tract of a human subject.

FIGS. 1 and 2 illustrate a nasal delivery device in accordance with a first embodiment of the present invention.

The delivery device comprises a housing 15, a nosepiece 17 for fitting in a nasal cavity of a subject, a mouthpiece 19 through which the subject in use exhales, and a substance supply unit 21, which includes an actuation member 23 which extends from one end of the housing 15 and is manually actuated to deliver substance to the nasal cavity of the subject.

The housing 15 includes a main body section 25, in this embodiment an elongate section, from one, base end of which extends the actuation member 23 of the substance supply unit 21.

The housing 15 further includes a grip section 27, which is disposed at the one end of the main body section 25.

The grip section 27 comprises a first, distal part 28 which includes at least one projecting grip element 29 by which a user grips the housing 15, typically between fingers, in actuating the actuation member 23 of the substance supply unit 21, and a second, proximal part 31 which provides a recess or waist 33 in which the fingers of the user are located.

In this embodiment the projecting grip element 29 is a circumferential flange or lip which extends around or substantially around the periphery of the housing 15.

The present inventors have recognized that the provision of the recess or waist 33 adjacent the flange or lip element 29 promotes proper orientation of the delivery device in the hand of the user, insofar as a user is required to orient the delivery device in a particular manner in the nasal cavity, in order to achieve optimal performance from the delivery device.

FIGS. 3 and 4 illustrate a nasal delivery device in accordance with a second embodiment of the present invention.

The delivery device of this embodiment is very similar to the above-described first embodiment, and thus, in order to avoid unnecessary duplication of description, only the differences will be described in detail.

In this embodiment the distal part 28 of the grip section 27 comprises first and second projecting grip elements 29*a*, 29*b*, which project to opposite sides of the housing 15, with no intermediate elements. In this embodiment the first and second projecting grip elements 29*a*, 29*b* are aligned on an axis common with that of the mouthpiece 19.

The present inventors have recognized that this configuration promotes a proper rotational orientation of the delivery device when gripped in the hand of a user, insofar as a user is required to orient the delivery device in a particular manner in the nasal cavity, in order to achieve optimal performance from the delivery device.

Finally, it will be understood that the present invention has been described in its preferred embodiments and can be modified in many different ways without departing from the scope of the invention as defined by the appended claims.

The invention claimed is:

1. A nasal delivery device for delivering substance to a nasal cavity of a subject, the delivery device comprising:
   a housing;
   a nosepiece for fitting to the nasal cavity of the subject;
   a mouthpiece configured for the subject to exhale through; and
   a substance supply unit, which includes an actuation member which extends from one end of the housing and is configured to be manually actuated to deliver substance to the nasal cavity of the subject;
   wherein the housing includes a main body section and a grip section;
      the grip section comprising:
         a first part which includes first and second projecting grip elements by which the subject grips the housing in actuating the actuation member of the substance supply unit, and
         a second part disposed between the main body section and the first part which provides a recess formed on an outer surface of the housing which extends around a periphery of the housing, the first and second projecting grip elements projecting to opposite sides of the housing, with no intermediate elements;
      whereby the recess promotes proper orientation of the delivery device in a hand of the subject.

2. The delivery device of claim 1, wherein the main body section comprises an elongate section.

3. The delivery device of claim 1, wherein the first and second projecting grip elements are radially aligned with the mouthpiece.

4. A method of delivering substance to a nasal cavity of a subject, the method comprising the steps of:
   providing a nasal delivery device, comprising:
      a housing;
      a nosepiece for fitting to the nasal cavity of the subject;
      a mouthpiece configured for the subject to exhale through; and
      a substance supply unit, which includes an actuation member which extends from one end of the housing and is configured to be manually actuated to deliver substance to the nasal cavity of the subject;
      wherein the housing includes a main body section and a grip section,
         the grip section comprising:
            a first part which includes first and second projecting grip elements by which the subject grips the housing in actuating the actuation member of the substance supply unit, and
            a second, proximal part disposed between the main body section and the first part which provides a recess formed on an outer surface of the housing which extends around a periphery of the housing, the first and second projecting grip elements projecting to opposite sides of the housing, with no intermediate elements;
   fitting the nosepiece to the nasal cavity of the subject;
   locating the mouthpiece in the mouth of the subject; and
   gripping the housing such that fingers of the subject are located in the recess at approximately opposite sides of the housing and adjacent the first and second projecting grip elements, thereby promoting proper orientation of the delivery device in a hand of the subject to effect operation of the delivery device.

5. The method of claim 4, wherein the main body section comprises an elongate section.

6. The method of claim 4, wherein the first and second projecting grip elements are radially aligned with the mouthpiece.

* * * * *